(12) United States Patent
Albany

(10) Patent No.: US 7,083,106 B2
(45) Date of Patent: Aug. 1, 2006

(54) LOCALLY STORING BIOLOGICAL SPECIMEN DATA TO A SLIDE

(75) Inventor: Peter Albany, Groton, MA (US)

(73) Assignee: CYTYC Corporation, Marlborough, MA (US)

( * ) Notice: Subject to any disclaimer, the term of this patent is extended or adjusted under 35 U.S.C. 154(b) by 178 days.

(21) Appl. No.: 10/656,092

(22) Filed: Sep. 5, 2003

(65) Prior Publication Data

US 2005/0051614 A1   Mar. 10, 2005

(51) Int. Cl.
*G06K 19/06* (2006.01)
(52) U.S. Cl. .............. 235/492; 235/375; 235/486; 382/133
(58) Field of Classification Search .......... 235/375, 235/486; 382/128, 134, 133
See application file for complete search history.

(56) References Cited

U.S. PATENT DOCUMENTS

| 5,561,556 A | * | 10/1996 | Weissman | 359/396 |
|---|---|---|---|---|
| 5,693,368 A | | 12/1997 | Ackerman et al. | |
| 6,198,299 B1 | * | 3/2001 | Hollman | 324/758 |
| 6,535,626 B1 | * | 3/2003 | Pressman et al. | 382/133 |
| 6,615,763 B1 | | 9/2003 | Edwards | |
| 6,631,203 B1 | * | 10/2003 | Ellis et al. | 382/128 |
| 6,905,823 B1 | * | 6/2005 | Kallioniemi et al. | 435/6 |

FOREIGN PATENT DOCUMENTS

| GB | 1 423 185 A | 1/1976 |
|---|---|---|
| WO | WO 97/22901 A | 6/1997 |
| WO | WO 99/10763 | 3/1999 |
| WO | WO 01/31566 A | 5/2001 |
| WO | WO 02/21425 A | 3/2002 |

OTHER PUBLICATIONS

Zebra Technologies Corp. RFID: The Next Generation of AIDC, Application White Paper. GSA#: GS-35F-0268N, 11315L Rev 4 (Sep. 2003).
PCT International Search Report for PCT/US2004/027439, Applicant: Cytyc Corporation, Forms PCT/ISA/210 and 220, dated Mar. 31, 2005 (6 pages).
PCT Written Opinion of the International Search Authority for PCT/US2004/027439, Applicant: Cytyc Corporation, Form PCT/ISA/237, dated Mar. 31, 2005 (5 pages).

* cited by examiner

*Primary Examiner*—Seung H Lee
(74) *Attorney, Agent, or Firm*—Vista IP Law Group

(57) ABSTRACT

An apparatus, system and method for analyzing biological specimens, including storing data relating to the analysis in a read/write data storage device attached to specimen carrier. The data storage device can be a Radio Frequency Identification (RFID) tag, a magnetic device, or a an optical device.

22 Claims, 5 Drawing Sheets

READER

LOCALLY STORING BIOLOGICAL SPECIMEN DATA TO A SLIDE

FIELD OF THE INVENTION

The present invention relates to the analysis of biological specimens, and more particularly, to storing and accessing data on a data storage device attached to a specimen carrier.

DESCRIPTION OF RELATED ART

Medical professionals and technicians often review biological specimens placed on viewing slides to analyze whether a patient has or may have a particular medical condition or disease. For example, a cytological specimen is examined to detect malignant or pre-malignant cells as part of a Papanicolaou (Pap) smear test and other cancer detection tests. To facilitate this review process, automated systems have been developed that focus the technician's attention on the most pertinent cells or groups of cells, while discarding less relevant cells from further review.

A typical automated system includes an imaging system and an automated optical microscope or review scope. The imaging system scans the specimen and generates images of sections of the specimen. These images are processed to identify the cells and cell clusters that are of diagnostic interest, which in some systems includes identifying those cells mostly likely have attributes consistent with malignant or pre-malignant cells, and their locations (x-y coordinates) on the slide. This information x-y coordinate information is provided to the microscope, which sequentially steps through the identified x-y coordinates, placing the cells or clusters of cells within the field of view of the technician. During the review, the technician may identify specific sections or images of the specimen that appear to be malignant or raise other concerns. These identified sections can be marked by the technician for further review.

X-Y coordinate data related to the analysis is transmitted to an external storage component, such as a database or server, that is accessed through an Ethernet or other network connection or to storage media, such as a Compact Disc (CD). Each patient test slide is assigned an identification number or other identifier. The slide is marked with the identification number, or a label with the identifier is applied to the slide. For example, a bar-code label with the identifier is applied to the slide or the technician can manually write the identifier on the slide using a marker.

The same identifier or number is used as a pointer in the database to link the stored images and data to the corresponding slide or specimen. For example, the identification number, reference coordinates, coordinates of specimen sections identified by the imaging system, and coordinates of specimen sections marked by a technician are transmitted by the imaging system or review scope over the network and to the database referenced by the identifier. The technician also connects to the database through the network to review or update the stored data.

Current data storage and management systems for biological specimens, however, can be improved. For example, a technician should be able to access slide and specimen data directly, without having to access and download data from an external database via a network. External databases and networks of conventional systems can also create problems if the database or network is temporarily inoperable. For example, the analysis of the specimen and reporting of the test results to concerned patients can be delayed as a result of database or network malfunctions or maintenance.

Storage capabilities and read/write options can also be improved. For example, a bar-code typically stores limited amounts of information, and even less information can be stored by manually marking a slide. Further, conventional systems typically are not able to overwrite or supplement existing data with new data. For example, with a bar-code, a technician may be required to print a new bar-code. With hand-written text or numbers, the old data is crossed out, and new data is written over the crossed-out data. Otherwise, a new slide must be prepared. These steps are inconvenient and time consuming.

Further, retrieving data from and storing data to an external database is inefficient compared to accessing data directly. Storage media, such as CDs, can also be misplaced or damaged, resulting in lost data and analysis. These shortcomings are amplified when hundreds or thousands of specimen slides are examined, as is often done by technicians and pathologists on a daily basis.

As a result of these shortcomings, the costs associated with analyzing a specimen are increased due to the database and network equipment and longer analysis times. Further, lost or destroyed data can result in repeated testing, increased processing times and inaccurate results. Databases and networks for storing slide and specimen data are also limiting since a technician is confined to conducting the analysis at a particular location that includes a particular imaging system and an optical microscope that are configured for network and database access.

In particular, it would be desirable to enable a technician to quickly and easily identify the sections of the specimen that warrant further analysis, regardless of the type of imaging and analysis equipment being used, and without dependence on the availability of a database and network connection.

SUMMARY OF THE INVENTION

In accordance with one aspect of the invention, apparatus for analyzing a biological specimen is provided with a means for locally storing data related to a biological specimen and/or its analysis. In one embodiment, the apparatus includes a biological specimen carrier, such as a slide, vial, bottle, or other container, and a read/write data storage device that is attached to the carrier. Data relating to the specimen and/or analysis of the specimen may be stored in, and be accessible from, the data storage device.

Other and further aspects and embodiments of the invention are described herein and will become apparent upon review of the following detailed description and drawings.

BRIEF DESCRIPTION OF THE DRAWINGS

Referring now to the drawings, in which like reference numbers represent corresponding parts throughout, and in which.

DETAILED DESCRIPTION OF PREFERRED EMBODIMENTS

Embodiments of a system and apparatus for providing necessary specimen and analysis information to a technician in an efficient manner, while eliminating the need to access such data through an external database and network, will now be described. The described system and apparatus allow for locally storing sufficient information on a biological specimen carrier to enable a technician to quickly and easily identify the sections of the specimen that warrant further analysis and allow the information on the slide to be locally updated as needed. In the following description, reference is made to the accompanying drawings, which show by way of illustration specific embodiments in which the invention may be practiced. It is to be understood that other embodiments may be utilized as various changes may be made without departing from the scope of the invention.

Figure 1:
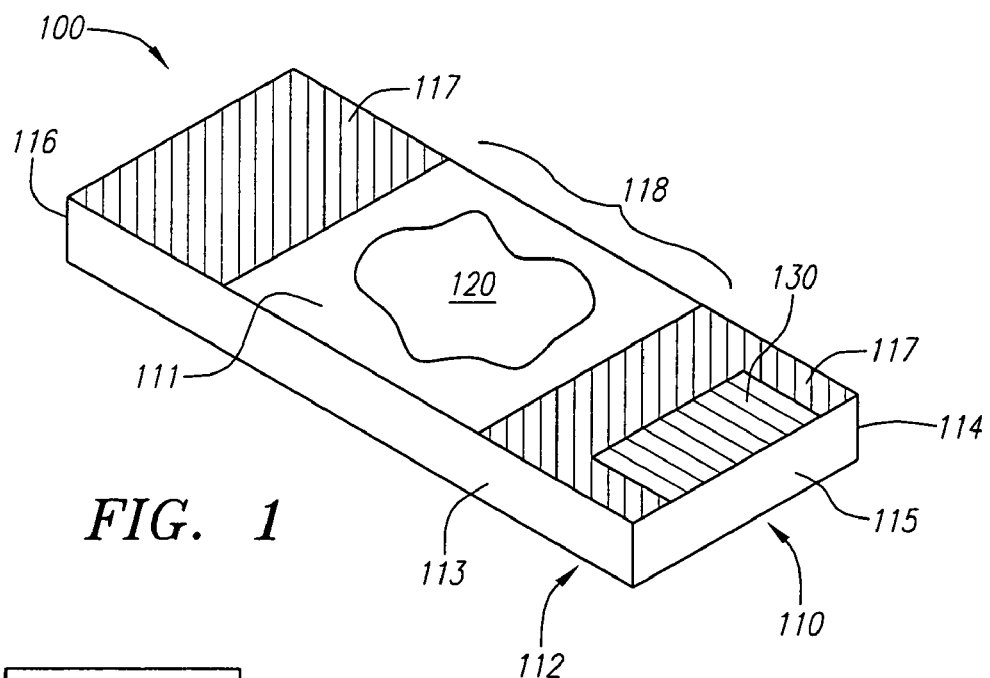
FIG. 1 is a perspective view of a data storage device attached to a biological specimen carrier, such as a test slide, according to the present invention.

Referring to FIG. 1, in accordance with the one aspect of the invention, an apparatus 100 for locally storing data related to analysis of a biological specimen includes a biological specimen carrier 110 with a specimen 120, and a data storage device 130 (shown generally as block 130) attached to the biological specimen carrier 110. The data storage device 130 can be attached directly or indirectly to the slide using, for example, an adhesive or a label. Persons of ordinary skill in the art will recognize that the inventive concepts and embodiments described herein can be utilized with different types of biological specimen carriers, specimens, data storage devices and analysis.

For example, the biological specimen carrier 110 can be a slide as shown in the Figures, such as a glass or plastic slide. The biological specimen carrier can also be a bottle, a vial, or other containers and objects for holding, storing or supporting a biological specimen. The biological specimen 120 can be a human cytological specimen that is analyzed to identify cancerous conditions or other medical conditions. The specimen 120 can also be an animal specimen that is analyzed by a veterinarian. For ease in illustration, the embodiments are described with reference to cytological (e.g., PAP smear) and other cancer-related specimens 120 of human patients on a slide. However, it should be appreciated that the invention is not so limited and can be utilized with the collection and analysis of various other specimens and biological specimen carriers.

Various types of data storage devices 130 can be used. The data storage device 130 can be a read-only or a read/write storage device and store different types of data. Exemplary data storage devices include, for example, a Radio Frequency Identification (RFID) tag, and magnetic and optical storage devices and media. The data can include, but is not limited to, data relating to the biological specimen, specific sections of the specimen, the carrier, the patient, the imaging equipment, the review or analysis equipment, and time and date data. Persons of ordinary skill in the art will recognize that other data can be stored to the storage device 130 depending on the particular patient, test, and analysis being performed. With this configuration, data can be locally stored in the data storage device 130 on the slide 110 and be accessed directly from the data storage device 130 without accessing an external database via a network connection. As a result, the data is readily available to a technician, and the specimen 120 can be analyzed more quickly and efficiently which, in turn, reduces the time and costs associated with PAP smears and other cancer analyses. Further, the apparatus 100 provides flexibility in the selection of the imaging and review equipment. For example, preferred embodiments of the invention allow for imaging and analysis of the specimen 120 to be conducted with various review and analysis equipment since it is not necessary to utilize specific imaging and analysis equipment that are proximately located or configured for a particular database and network connection.

Further, the data storage device 130 can be attached to different sections or locations of the slide 100. For example, the data storage device 130 can be attached to a top surface 111, a bottom surface 112, a first side 113, a second or opposite side 114, a first edge 115, a second or opposite edge 116 and end sections 117. Top surfaces of some slides include "frosted" end sections 117 that provide higher friction surfaces and allow a technician to handle the slide more easily. As shown in FIG. 1, the data storage device 130 is attached to an end section 117 or top surface 111 of the slide 110, but the invention is not so limited since different storage devices 130 may be suitable for other slide 110 locations. The specimen 120 is typically placed in a middle or specimen section 118 between the ends of frosted sections 117 of the slide 110, but the specimen 120 can also be placed at an end 117 of the slide 100 so that an opposite end is handled by a technician. Accordingly, the configuration shown in FIG. 1 is merely illustrative of different possible specimen 120 and data storage device 130 arrangements.

Figure 2A:
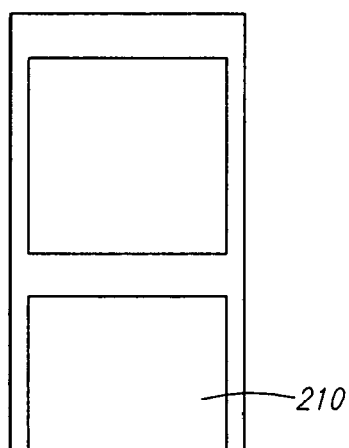
FIG. 2A illustrates a Radio Frequency Identification (RFID) data storage device that is embedded in an adhesive label that is attached to a biological specimen carrier.

Referring to FIG. 2A, one exemplary data storage device 130 that is attached to the test slide 100 is a Radio Frequency Identification (RFID) tag or transponder 200. Various RFID tags 200 are suitable, such as a Tag-IT ® RFID tag available from Texas Instruments, Radio Frequency Identification Systems, 6550 Chase Oaks Blvd., MS 8470, Plano, Tex. 75023 or an Intellitag® label having an RFID insert, available from Intermec Technologies Corporation, Identification Systems Division, 9290 LeSaint Drive, Fairfield, Ohio 45104. These exemplary RFID 200 devices are preferably embedded in a label 210, as shown in FIG. 2A, which is attached to the slide 110. The RFID tag 200 can also be attached to a slide in different manners, for example, by using a protective coating (not shown) that is applied over the RFID tag 200 to secure the RFID tag 200 to the slide 110. Various adhesives can also be utilized to attach the RFID tag 200 to the slide 110.

Figure 2B:
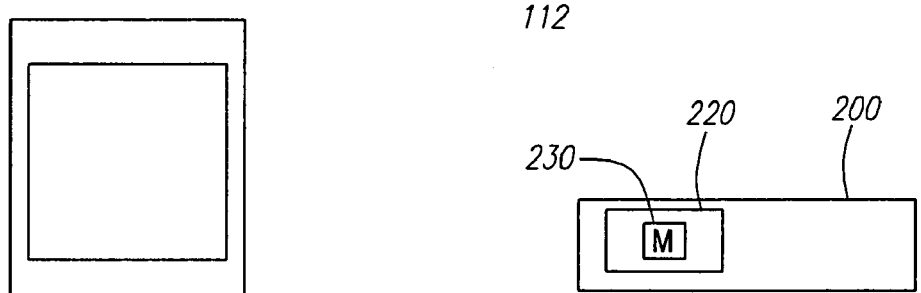
FIG. 2B illustrates components of a typical RFID tag.

Referring to FIG. 2B, a RFID tag 200 typically includes an Integrated Circuit (IC) 220, such as an Application Specific Integrated Circuit (ASIC), that includes a memory 230 for storing data. Different sizes of memories 230 can be used to store different amounts of specimen information.

Figure 2C:
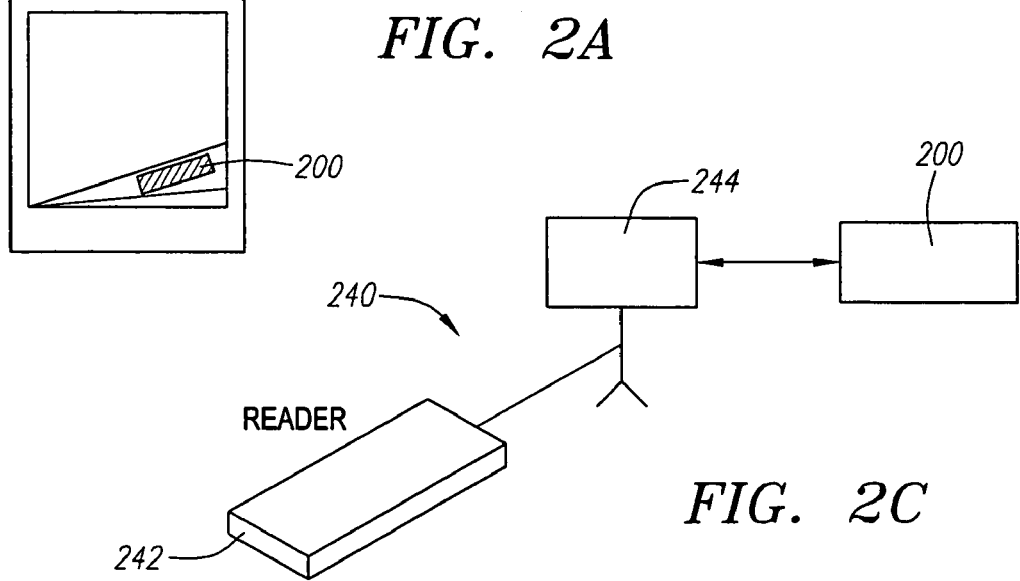
FIG. 2C illustrates a typical RFID tag system.

Referring to FIG. 2C, a typical RFID tag system 240 includes the RFID tag 200, as previously discussed, a reader 242, and an antenna 244. The RFID tag 200 is activated by an instruction or signal from the reader 242, which is sent through the antenna 244. For example, the reader 242 sends a signal to the IC 220 via the antenna 310 to wirelessly write data to or read data from the memory 230 of the IC 210. In use, a user is usually permitted to activate the RFID tag 200 to read data from the memory 230. Data can also be written to the memory 230 depending on the read/write configuration of the memory 230. Further, data stored in the memory 230 can be updated to supplement or overwrite existing data depending on the memory 230 configuration. Further, the RFID tag 200 can be attached to various slide 100 surfaces and locations since a line of sight between the RFID tag 200 and reader 230 is not necessary. Preferably, the RFID tag 200 is attached to a top end 117 of a slide 110 so that the tag 200 does not interfere with the analysis of the specimen 120.

Figure 3:
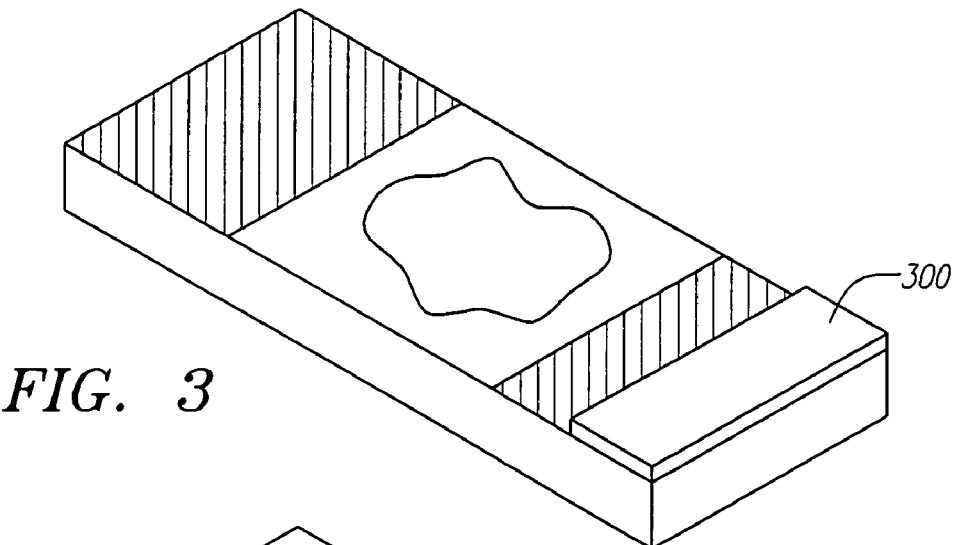
FIG. 3 illustrates a magnetic data storage device attached to a biological specimen carrier.

Referring to FIG. 3, in an alternative embodiment, the data storage device 130 is a magnetic media 300. Persons of ordinary skill in the art will recognize that various magnetic storage devices 300 can be utilized. Exemplary magnetic devices 300 include magnetic encoded strips, available from ID Tech, 1047 South Placentia Avenue, Fullerton, Calif. These exemplary magnetic coded strips and related readers are based encoding characteristics based on ANSI, and ISO/IEC Standards and can store various types of alpha-numeric specimen data.

Figure 4A:
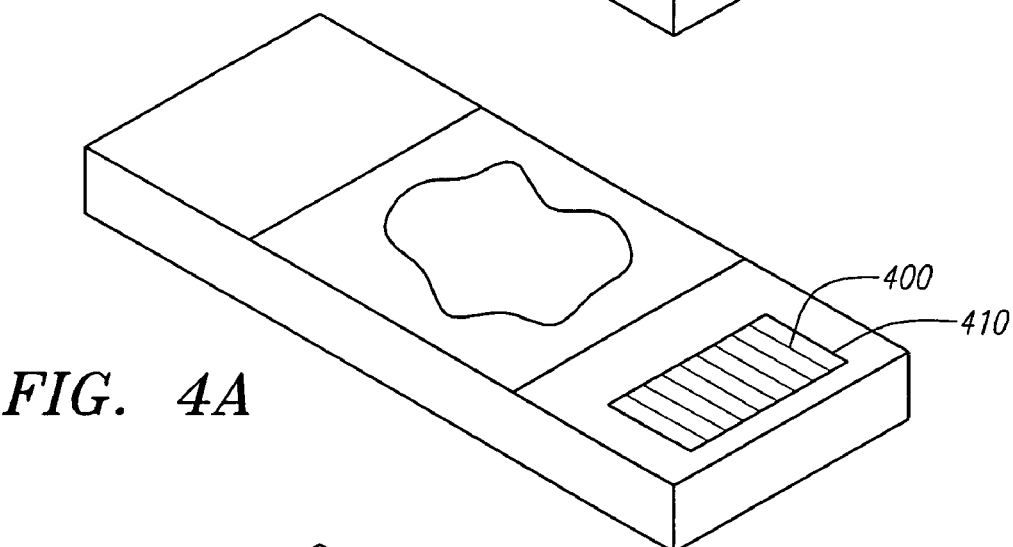
FIG. 4A illustrates an optical storage device in the form of a bar-code label attached to a biological specimen carrier.
Figure 4B:
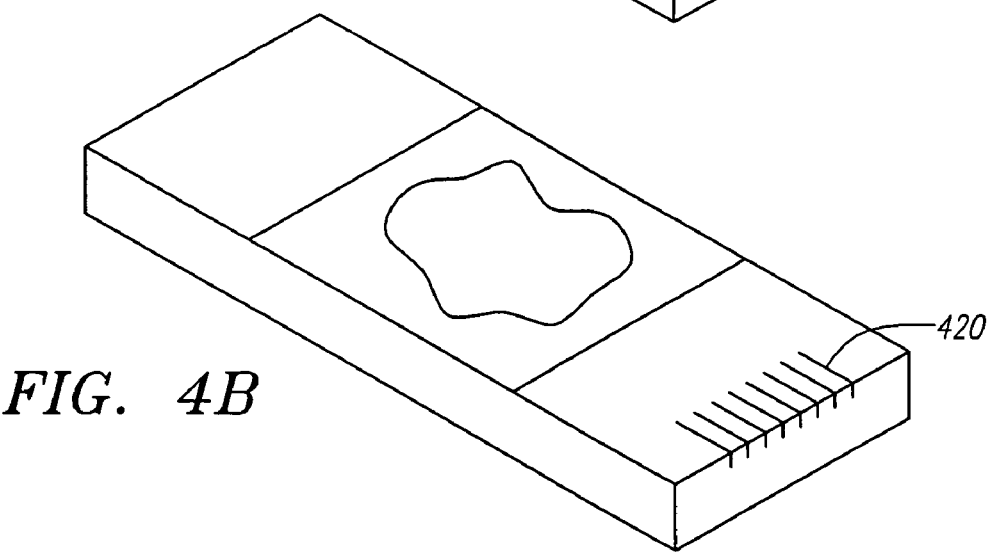
FIGS. 4B–C illustrate an optical data storage device in the form of etchings formed within a surface of a biological specimen carrier.
Figure 4C:
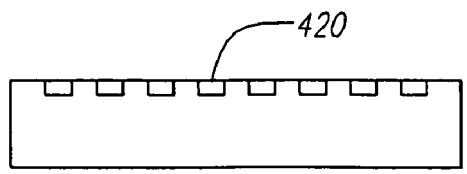

Referring to FIGS. 4A–C, in a further alternative embodiment, the data storage device 130 is an optical data storage device. One exemplary optical data storage device is a bar-code 400 or other binary modulation symbol or device, as shown in FIG. 4A. The bar-code 400 can be printed on an adhesive label 410, which is attached to the slide 110, e.g., at an end 117 of the slide 110. Alternatively, as shown in FIGS. 4B–C, a surface of the slide 110 can be marked or etched 420 with information. For example, the etchings 420 can be lines, patterns, text or numbers 420 that contain or represent different types of cytological or biological specimen information.

Figure 5A:
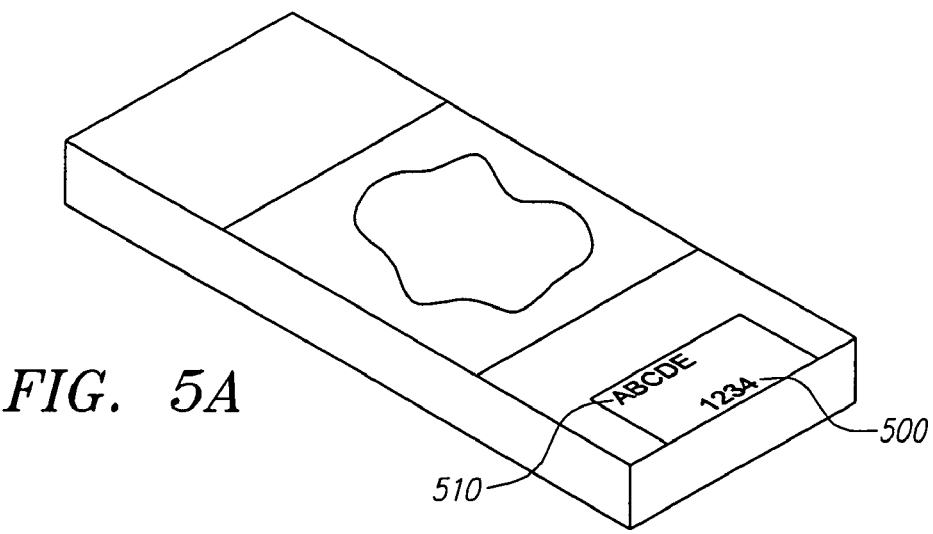
FIGS. 5A–B illustrate a label with printed carrier or specimen information that is attached to a biological specimen carrier.
Figure 5B:
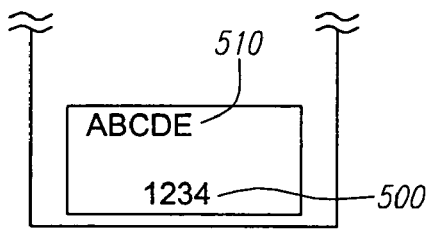

As shown in FIGS. 5A–B, specimen information can also be printed directly onto a label 500, which is then attached to a slide 110. Different letters, numbers, symbols or other markings 510 can be typed in a sufficiently small font or symbology to fit on the label 500. The markings 510 can be readable by the naked eye or with the assistance of a magnification device, such as a magnifying glass or microscope. The size of the markings 510, and thus, the quantity of information stored on the label 500, can be increased or decreased depending on the amount of information to be stored on the slide 110 and the available viewing devices.

Data storage devices 130 can include different amounts of memory to store different quantities of data. Further, data storage devices can be configured to write and/or read data to/from the data storage device in the even that stored data is to be updated or supplemented. Thus, embodiments of present invention provide enhanced data storage capabilities and read/write options.

Figure 6:
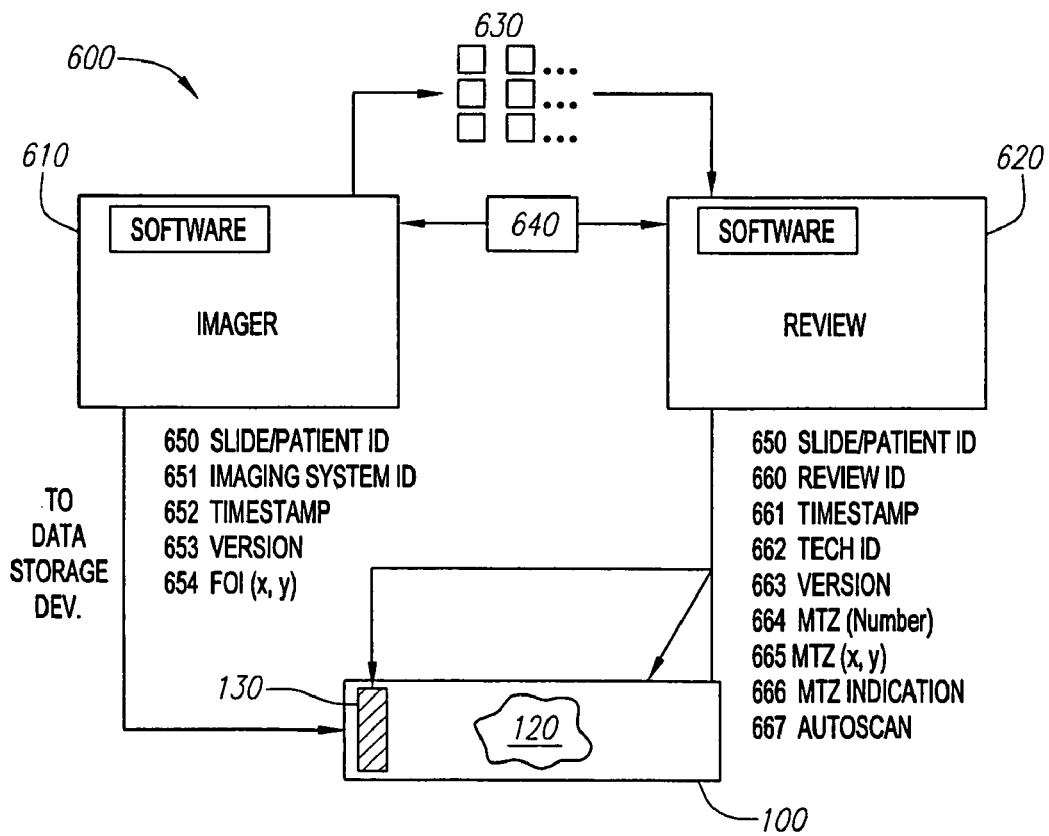
FIG. 6 shows a system for generating and analyzing specimen images and locally storing and retrieving data to a data storage device attached to a biological specimen carrier.

Having described various exemplary data storage devices 230 that can be used with the apparatus 100, FIG. 6 generally illustrates a system 600 for generating and analyzing images of a specimen 120, and storing data to and retrieving data from a storage device 130 attached to a slide 100. An exemplary system 600 includes the slide 110 with a data storage device 130, as previously described, an imaging device or system 610, and an automated or semi-automated review device or system, such as a microscope 620 or other suitable device.

The imaging system 610 scans the specimen 120 and generates or prepares a series of images 630 of sections of the specimen 120 utilizing, for example, a software program 612. The system 600 can also include if necessary, a filter or processor 640 that eliminates extraneous data from the images 630 before they are reviewed using the microscope 620. Different types of information and data related to the imaging system 610 can be recorded to the data storage device 230 including, but not limited to, a slide, patient or specimen identifier 650 (if not assigned already), such as an alpha, numeric, or alpha-numeric identifier, imaging system identifier 651, a timestamp 652 representing a date and time that the images 630 were generated with the imaging system 610, a version 653 of the imaging system software 612 that was used to generate the images 630, and coordinates (x,y) of Fields Of Interest (FOIs) 654, described below.

Figure 7:
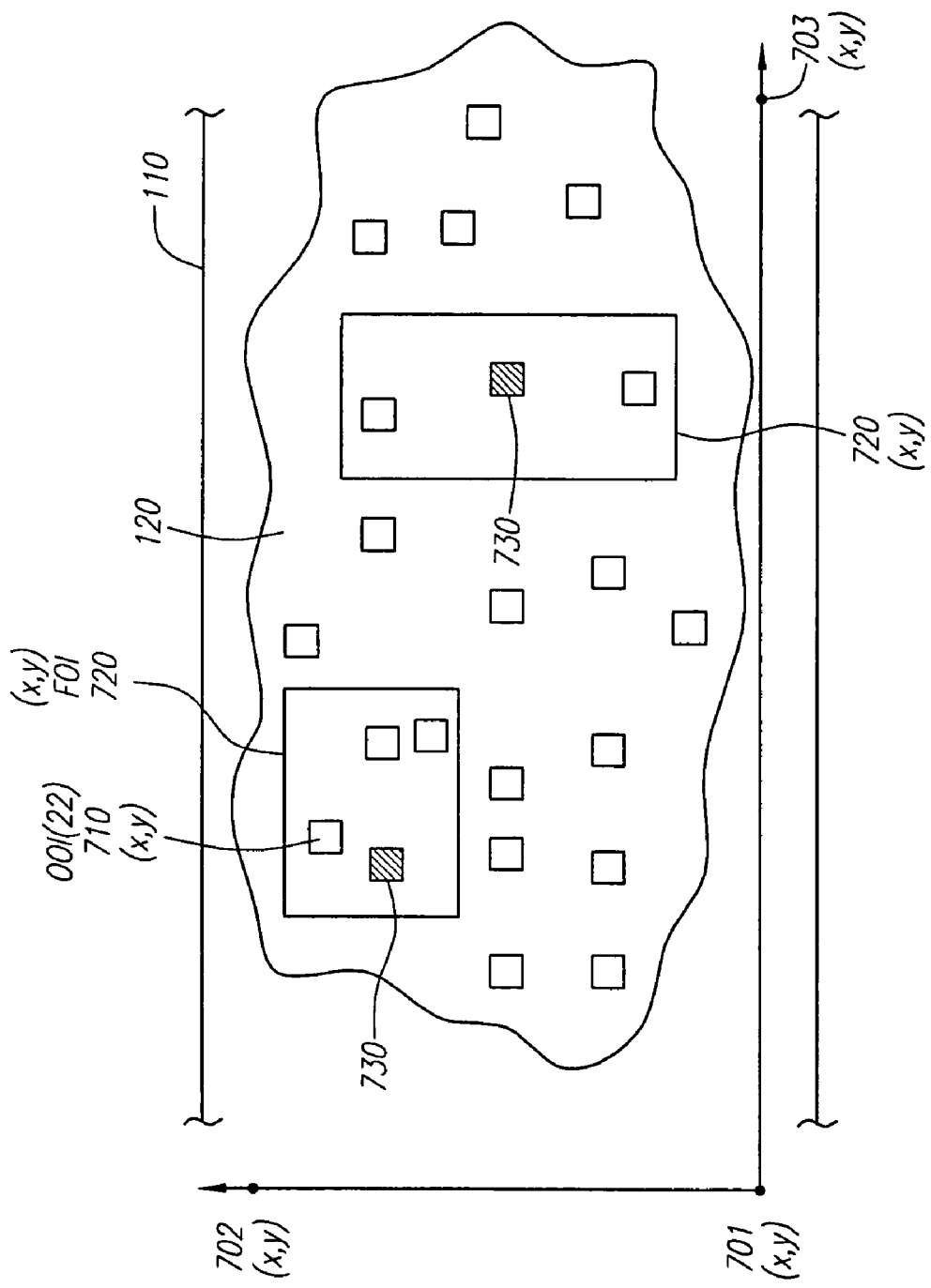
FIG. 7 shows how images or objects of interest can be organized for review by a technician.

Referring to FIG. 7, an exploded view of the slide specimen 120, the imaging system 610 also establishes a reference or fiduciary coordinate system 700 within which sections of the specimen 120 can be identified. More specifically, the imaging system 610 allocates three fiducial marks that establish the reference coordinate system: (X0, Y0) 701; (X1, Y1) 702; and (X2, Y2) 703. These three coordinates 701-703 establish a reference grid 700, with coordinate 701 representing x=0, y=0. The images 630 of sections of the specimen 120 are mapped against the reference grid 700.

The imaging system 610 also processes or analyzes images 630 to identify and select images having cells and cell clusters that most likely have attributes that warrant further consideration by a Cytotechnologist. In one embodiment, these attributes may be those that are consistent with malignant or pre-malignant cells. In either case, these identified cells may be referred to as Objects of Interest (OOI) 710. The image analysis can be performed using, for example, a processor implemented program. One or more OOIs 710 can be organized within a defined boundary or Field Of Interest (FOI) 720. A FOI 720 can be defined in various ways and with various geometries to include different numbers of OOIs 710. For example, a FOI 720 can have shapes and dimensions, such as rectangles, ellipses, triangles, and polygons, that cover different portions of the specimen 120 and different numbers of OOIs 710. FIG. 7 shows FOIs as squares or rectangles for purposes of illustration. Thus, four (x,y) coordinates can be used to identify the boundaries of each FOI.

An OOI 710 can be assigned to a FOI 720 based on different criteria. For example, an OOI 710 can be assigned to an FOI 720 if the subject OOI 710 was not previously assigned to an FOI 720. An FOI 720 can also be defined to include all of the OOIs 710, or to maximize or minimize the number of OOIs 720 in a limited FOI 720. OOIs 710 can also be ranked based on, for example, the likelihood that the OOI 710 includes cells of diagnostic interest, and can be selected for inclusion in a particular FOI 720 based on the ranking. In one embodiment, the analysis system 610 establishes 22 FOIs 720, i.e., 22 (X,Y) coordinates, relative to the reference coordinate system 700, that identify or define the FOIs 720 with one or more OOIs 710.

A technician analyzes the OOIs 710 organized or allocated to the 22 FOIs 720 with the microscope 620, which proceeds or steps through the x-y coordinates of each FOI 720 identified by the imaging system 610 and places them within the field of view of the technician. In a preferred embodiment, the order in which FOIs are presented for review is governed by a version of a so-called "traveling salesman" algorithm, resulting in the least amount of movement of the microscope stage. During the review, the technician may identify specific FOIs 720 that are likely to contain malignant or pre-malignant cells or raise other concerns. The coordinates of these identified FOIs 720 can be marked or highlighted by the technician and are referred to as Marked Target Zones (MTZs) 730.

Referring again to FIG. 6, different types of information related to reviewing and analyzing the images 630 can also be stored in the data storage device 130 on the slide 110, including but not limited to, the slide or patient identifier 650, an identifier 660 of the review scope 620, a timestamp 661 with the date and time indicating when the review scope 620 was utilized, an identification 662 of the technician who performed the review scope analysis 620, a version 663 of the review scope software 662, a number of MTZs 664, coordinates 665 of MTZs, an indication 666 of whether the MTZ 730 falls within a FOI 720, and whether an autoscan 667 was conducted. Additional information on systems and methods of reviewing and analyzing slide specimens may be found in U.S. Pat. No. 6,562,299, which is assigned to the assignee of the present invention, the entire disclosure of which is expressly incorporated by reference herein.

Figure 8:
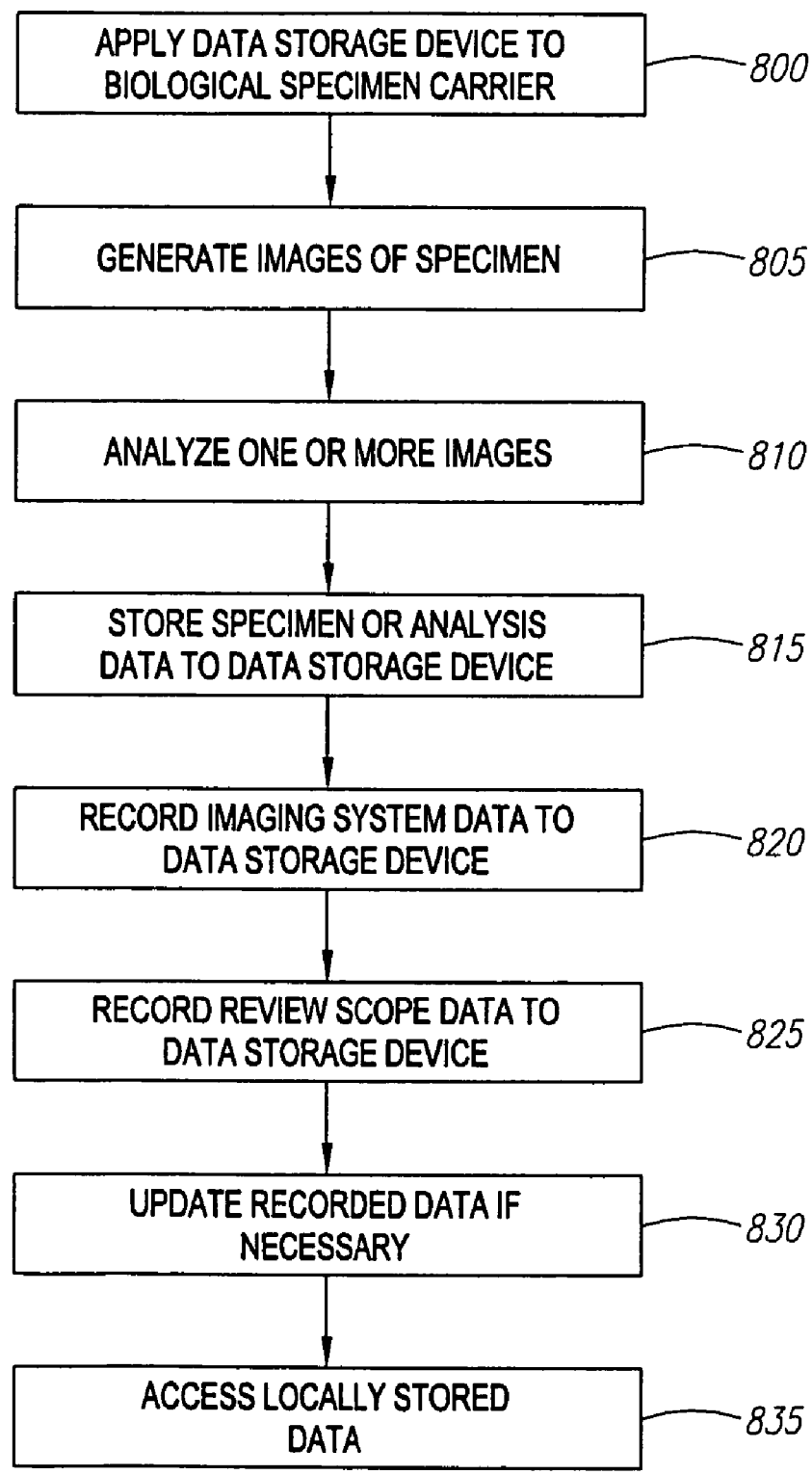
FIG. 8 is a flow diagram illustrating a method of generating and analyzing specimen images and locally storing and retrieving data from a data storage device attached to a biological specimen carrier.

Referring to FIG. 8, having described various configurations of an exemplary apparatus and an exemplary system of the invention, a description of the method of locally storing data related to specimen analysis to and reading the data from a data storage device attached to a test slide is provided. Initially, in step 800, a data storage device is attached to a biological specimen carrier, such as a slide. For example, the data storage device can be attached to a label which is applied to the slide, or attached with a coating or an adhesive. In step 805, a plurality of images of the specimen are generated by the imaging system. In step 810, one or more images of the plurality of images are analyzed. In step 815, data relating to the specimen or specimen analysis is locally stored to the data storage device such as, for example, a specimen or slide identifier, data related to an imaging system (e.g., identifier, software version, timestamp), and data related to a review system or review of the specimen (e.g., identifiers of the technician and review system, software version, timestamp, Fields of Interest, coordinates, Marker Target Zones). In step 820, data from an imaging system is recorded to the data storage device. In step 825, data from a review scope is recorded to the data storage device. In step 830, the recorded data can be updated as needed. In step 835, the locally stored data in the storage device can be accessed by a technician without connecting to an external database or network.

The previously described apparatus, system and method embodiments of the invention provide a number of enhancements to conventional test slides, slide imaging and analysis systems, and analysis processes, which eliminate the need to access an external database or separate media device such as a CD, to retrieve necessary slide, specimen or analysis data. Instead, these embodiments of the invention allow a technician to directly access pertinent carrier and specimen data that is stored locally on the slide. As a result, a technician can analyze specimen images more efficiently. Further, since the slide with a data storage device can serve as a "self-contained database," the slides can be moved between laboratories and be analyzed in different locations without the restrictions associated with external databases and network equipment. The data stored on the slide can also be supplemented and updated as needed.

Persons of ordinary skill in the art will recognize that aspects of the invention can be modified in various ways. For example, other data storage devices can be attached to a slide to store pertinent slide and specimen data. Further, such embodiments allow various types and quantities of data to be locally stored on the slide. Accordingly, persons of ordinary skill in the art will appreciate that the invention is not limited to the particular exemplary embodiments described and illustrated, but that insubstantial modifications, alterations, and substitutions can be made to the described embodiments without departing from the scope of the invention, as recited in the accompanying claims.

What is claimed:

1. Apparatus for analysis of a cytological specimen, comprising:
   a cytological specimen carrier; and
   a read/write data storage device attached to the carrier,
   wherein data including a coordinate of a field of interest related to cellular analysis of the cytological specimen carried in or on the carrier may be stored in, and retrieved from, the data storage device.

2. The apparatus of claim 1, the cytological specimen carrier comprising a slide.

3. The apparatus of claim 1, the cytological specimen carrier comprising a vial.

4. The apparatus of claim 1, the data storage device comprising a radio frequency identification device.

5. The apparatus of claim 1, the data storage device comprising a magnetic storage device.

6. The apparatus of claim 1, the data storage device comprising an optical storage device.

7. The apparatus of claim 1, wherein the data related to the analysis of the cytological specimen is an identifier or a timestamp.

8. A system for analyzing a cytological specimen, comprising:
   a cytological specimen carrier;
   an imaging device configured to obtain images of a cytological specimen carried in the carrier;
   a processor implemented program for analyzing images of the specimen obtained by the imaging device and for identifying objects in the specimen from the images;
   a microscope for viewing objects in the specimen identified by the processor implemented program; and
   a read/write data storage device attached to the cytological specimen carrier,
   wherein data including a coordinate of a field of interest related to an analysis of the cytological specimen may be stored in or on, and retrieved from, the data storage device.

9. The system of claim 8, the cytological specimen carrier comprising a slide.

10. The system of claim 8, the cytological specimen carrier comprising a vial.

11. The system of claim 8, the data storage device comprising a radio frequency identification device.

12. The system of claim 8, the data storage device comprising a magnetic storage device.

13. The system of claim 8, the data storage device comprising an optical storage medium.

14. The system of claim 8, wherein the data related to the analysis of the specimen includes an identifier or a timestamp.

15. A method for analyzing a cytological specimen, comprising:
   providing a cytological specimen in or on a cytological specimen carrier;
   storing data related to cellular analysis of the cytological specimen in a read/write data storage device attached to the cytological specimen carrier;
   obtaining images of the cytological specimen; and
   analyzing the images with a processor implemented program, wherein the stored data comprises a location of an object of interest in the cytological specimen that was identified by the image analysis.

16. The method of claim 15, the data storage device comprising a radio frequency identification device.

17. Apparatus for analysis of a cytological specimen, comprising:
    a cytological specimen carrier; and
    a read/write data storage device attached to the carrier,
    wherein data including a coordinate of a marked target zone related to the cellular analysis of the cytological specimen carried in or on the carrier may be stored in, and retrieved from, the data storage device.

18. A system for analyzing a cytological specimen, comprising:
    a cytological specimen carrier;
    an imaging device configured to obtain images of a cytological specimen carried in the carrier;
    a processor implemented program for analyzing images of the specimen obtained by the imaging device and for identifying objects in the specimen from the images;
    a microscope for viewing objects in the specimen identified by the processor implemented program; and
    a read/write data storage device attached to the cytological specimen carrier,
    wherein data including a coordinate of a marked target zone related to the analysis of the cytological specimen may be stored in or on, and retrieved from, the data storage device.

19. A method for analyzing a cytological specimen, comprising
    providing a cytological specimen in or on a cytological specimen carrier;
    storing data including a coordinate of a field of interest or a coordinate of a marked target zone related to the cellular analysis of the cytological specimen in a read/write data storage device attached to the cytological specimen carrier.

20. A method for analyzing a cytological specimen, comprising
    providing a cytological specimen in or on a cytological specimen carrier;
    storing data including a coordinate of a marked target zone related to the cellular analysis of the cytological specimen in a read/write data storage device attached to the cytological specimen carrier.

21. A system for analyzing a cytological specimen, comprising:
    a cytological specimen carrier;
    an imaging device configured to obtain images of a cytological specimen carried in the carrier;
    a processor implemented program for analyzing images of the specimen obtained by the imaging device and for identifying objects in the specimen from the images;
    a microscope for viewing objects in the specimen identified by the processor implemented program; and
    a read/write data storage device attached to the cytological specimen carrier,
    wherein data including coordinates of locations of identified objects in the cytological specimen related to an analysis of the cytological specimen may be stored in or on, and retrieved from, the data storage device.

22. A system for analyzing a cytological specimen, comprising:
    a cytological specimen carrier;
    an imaging device configured to obtain images of a cytological specimen carried in the carrier;
    a processor implemented program for analyzing images of the specimen obtained by the imaging device and for identifying objects in the specimen from the images;
    a microscope for viewing objects in the specimen identified by the processor implemented program; and
    a read/write data storage device attached to the cytological specimen carrier,
    wherein data including cellular analysis data related to an analysis of the cytological specimen may be stored in or on, and retrieved from, the data storage device.

* * * * *